United States Patent
Berrevoets

(10) Patent No.: US 8,343,165 B2
(45) Date of Patent: Jan. 1, 2013

(54) APPARATUS AND METHOD FOR IMPLANTATION OF SURGICAL DEVICES

(75) Inventor: Gregory Berrevoets, Skandia, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 901 days.

(21) Appl. No.: 12/088,104

(22) PCT Filed: Sep. 26, 2006

(86) PCT No.: PCT/US2006/037789
§ 371 (c)(1),
(2), (4) Date: Oct. 21, 2008

(87) PCT Pub. No.: WO2007/038654
PCT Pub. Date: Apr. 5, 2007

(65) Prior Publication Data
US 2009/0163963 A1    Jun. 25, 2009

Related U.S. Application Data

(60) Provisional application No. 60/720,955, filed on Sep. 26, 2005.

(51) Int. Cl.
*A61B 17/58* (2006.01)
(52) U.S. Cl. .......... 606/104; 606/86 A; 606/99; 81/444
(58) Field of Classification Search .......... 606/86 A, 606/91, 99, 104, 916; 81/436–461
See application file for complete search history.

(56) References Cited

U.S. PATENT DOCUMENTS

| | | | | |
|---|---|---|---|---|
| 4,553,455 A | * | 11/1985 | Wilcox et al. | 81/443 |
| 5,171,243 A | * | 12/1992 | Kashuba et al. | 606/86 R |
| 5,515,755 A | * | 5/1996 | Kung | 81/452 |
| 5,649,931 A | * | 7/1997 | Bryant et al. | 606/104 |
| 5,667,513 A | * | 9/1997 | Torrie et al. | 606/104 |
| 6,082,233 A | * | 7/2000 | Han | 81/453 |
| 6,857,343 B1 | * | 2/2005 | Easterbrooks et al. | 81/452 |
| 7,473,255 B2 | * | 1/2009 | McGarity et al. | 606/86 B |
| 7,491,208 B2 | * | 2/2009 | Pond et al. | 606/104 |
| 7,650,991 B2 | * | 1/2010 | Hester et al. | 206/339 |
| 7,651,502 B2 | * | 1/2010 | Jackson | 606/99 |
| 2003/0233095 A1 | * | 12/2003 | Urbanski et al. | 606/72 |
| 2005/0261691 A1 | * | 11/2005 | Hester et al. | 606/73 |
| 2006/0111713 A1 | * | 5/2006 | Jackson | 606/61 |
| 2007/0162009 A1 | * | 7/2007 | Chao et al. | 606/61 |
| 2008/0045955 A1 | | 2/2008 | Berrevoets et al. | |

* cited by examiner

*Primary Examiner* — Alvin Stewart
*Assistant Examiner* — Jerry Cumberledge
(74) *Attorney, Agent, or Firm* — Fitch, Even, Tabin & Flannery, LLP

(57) ABSTRACT

A driver apparatus for implanting spinal rod fixation devices including an anchor member and a coupling member pivotable relative to the anchor member is disclosed. The driver apparatus generally immobilizes the anchor member and coupling member relative to each other and to the driver apparatus during insertion to minimize interference between the coupling member and tissues surrounding the implantation site, as well as to minimize the clearance required for implantation. The driver apparatus includes a driver portion engageable with the anchor member for effecting seating of the anchor member, such as by threadably driving the anchor member in the bone. The driver portion is closely fit between portions such as upstanding walls of the coupling member to prevent relative rotation therebetween. The driver apparatus further includes locking portions shiftable to secure the coupling member with the driver apparatus when the driver is engaged with the anchor member.

7 Claims, 12 Drawing Sheets

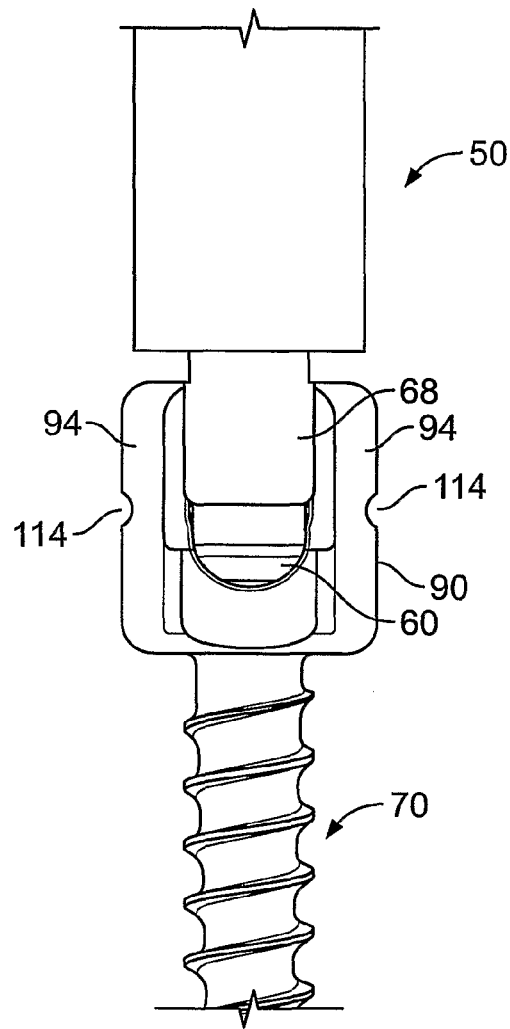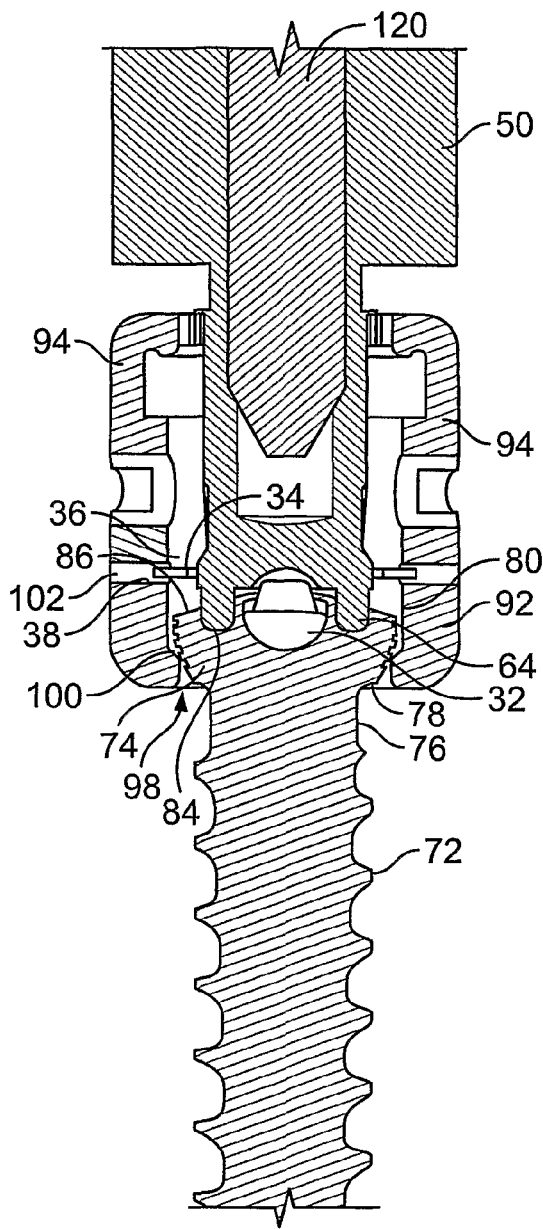
FIG. 9
FIG. 10

APPARATUS AND METHOD FOR IMPLANTATION OF SURGICAL DEVICES

CROSS-REFERENCE TO RELATED APPLICATIONS

This application is a U.S. national phase application filed under 35 U.S.C. § 371 of International Application PCT/US2006/037789, filed on Sep. 26, 2006, which claims priority from U.S. Provisional Application No. 60/720,955, filed on Sep. 26, 2005, which are hereby incorporated herein by reference in their entirety.

FIELD OF THE INVENTION

The invention relates to An apparatus and method for implanting surgical devices, in particular, for implanting and securing a fixation device to a bone, and, more particularly, to a driving apparatus and method for implanting an anchor of a spinal rod fixation device in a bone.

BACKGROUND OF THE INVENTION

There are currently a wide array of surgical devices for spinal surgery. One group of these devices includes a fixation device including a screw or hook anchor for securing the device to a vertebrae, such as the pedicle portion of the vertebra. Many of these surgical devices are spinal rod fixation devices and include a coupling portion for receiving or otherwise securing a spinal rod or other elongated member relative to the anchor. Commonly, the coupling portion or yoke is a distinct member from the anchor so that they can take on a plurality of different orientations relative to each other.

For example, for a screw anchor member, a threaded shank of the screw anchor is driven into the pedicle portion at a particular angle. At times, the orientation and position of the threaded shank with the vertebra is dictated by the surface geometry or other characteristics particular to the patient and/or to the individual vertebrae. However, the spinal rod that is to be coupled with and fixed relative to the screw anchor has a configuration and position that is dictated more by the goals of the medical procedure. To allow the yoke to receive the spinal rod, while also permitting the desired positioning of the spinal rod, the yoke member may assume a number of orientations relative to the screw anchor so that their respective axes are other than in alignment with each other.

During installation, this polyaxial feature presents a number of issues. The coupling member is not secured relative to the screw anchor during insertion. Thus, the coupling member tends to pivot by its own weight as the screw is being driven into the vertebral bone. This can be problematic as the coupling member may interfere with the rotational driving action, such as by binding with the driver and screw anchor, and this interference may inadvertently alter the position and orientation in which the shank is driven.

It is desired to minimize the resection required to implant the fixation device and its associated coupling member. In the event that the coupling member tilts or pivots from alignment with the axis of the screw anchor, the coupling member may contact tissues surrounding the implantation site for the fixation device. As the screw member turns with the coupling member tilted to one side, the coupling member may sweep around the implantation site potentially causing damage to surrounding tissues. As is apparent, the polyaxial movement provided between the screw anchor and yoke coupling member can make the driving operation for implanting the screw into the vertebral bone more difficult than is desired.

In general, it is preferred to minimize the incision and resection performed on a patient for most operations. For instance, arthroscopy and endoscopes were developed to permit inspection and surgery for interior anatomical portions while avoiding significant incisions through healthy and non-damage tissues. As such, it is also desired to minimize the size of the fixation device including the coupling member thereof during implantation.

There are numerous tools devised for implanting the various designs of fixation devices and coupling devices. A prior art device is further known for seating a screw in the pedicle portion of a vertebrae, the screw having an associated coupling device, wherein the prior art device generally stabilizes the coupling device relative to the screw during driving. More specifically, U.S. Pat. No. 6,858,030, to Martin, et al., discloses a driver for implanting a screw of a pedicle screw assembly that includes a polyaxial coupling element. The driver has threads spaced up along its shaft from the lower driver end for being received in internal threads formed along the inner surface of the walls of the coupling element. Internally threading these walls necessitates that the walls be of sufficient thickness for forming threads therein, undesirably increasing the size or width of the coupling element, as well as the height of these walls along which the threads are formed. Seating of the drive prongs in the corresponding recesses of the screw head is difficult due to the need to positively thread the driver into the coupling element. Further, after the screw has been fully implanted in the pedicle of the vertebra, releasing the driver requires it be turned to back the shaft threads out from the coupling element threads, potentially loosening the implanted screw.

In fact, the driver and screw head of the '030 patent require a linear engagement, while the shaft is rotated into the coupling element. To achieve this, the coupling element must be rotated relative to both the driver and the screw so that they are drawn together (or forced away) by the coupling element. Disconnection of the shaft and coupling element would require a surgeon's fingers, or another device, reaching into the implant site and rotating the coupling element a plurality of revolutions.

Accordingly, there is a need for a device for an optimized apparatus and method for implanting screw and anchor members of spinal rod fixation devices having a polyaxial coupling member in terms of the ease in which the screw anchor is driven into the vertebral bone. In addition, an apparatus and method for implanting screw anchors is desired that keeps the size of the device, and in particular the coupling member, to a minimum.

SUMMARY OF THE INVENTION

In accordance with one aspect, an apparatus is disclosed for securing with and generally immobilizing in a pre-determined relative orientation an anchor or screw and a pivotable coupling member of a surgical device such as a spinal rod fixation device. In this manner, the coupling device and fixation device can be secured joined or driven into a bone such as a vertebrae without the coupling device and fixation device pivoting relative to each other. By restricting or eliminating the pivoting of the components of the surgical device, the size of the incision into the anatomy and through the surrounding tissues can be minimized, and damage to surrounding tissues as a result of rotating the surgical device is minimized.

Each of the coupling device and fixation device has a central longitudinal axis. When secured with the implantation device, the respective longitudinal axes are aligned with each other. The implantation device is received within the coupling device and fixation device so that it does not substantially exceed the profile and size of the surgical device itself. Thus, the surgical device has a single longitudinal axis, and the radial extent of the surgical device is generally that of the components of the surgical device and, typically, the radial extent of the coupling device. Again, securing the components of the surgical device with the implantation device in such a manner minimizes the size of the incision and resection of surrounding tissues.

The implantation device also retains the surgical device. During a surgical implantation procedure, the surgical device must be guided through openings made in the surrounding tissues. The implantation device forms a mechanical connection with the surgical device so that, while being manipulated, the surgical device does not separate or fall off the implantation device. As the fixation device is often a screw, a typical screw and screwdriver cooperation commonly requires a surgeon's hand to hold the screw in engagement with the screwdriver at least until the screw tip is position at a bone surface for receiving the screw therein. The implantation device retains the surgical device, once secured therewith, until it is desired to release the surgical device, such as post-implantation.

With a typical screw and screwdriver cooperation, it is also commonly necessary for a surgeon's hand to position the screw tip at a desired implantation point or region, and to maintain the screw in proper alignment during at least an initial driving of the screw into a bone. The implantation device with the surgical device secured thereto allows a surgeon to use a second, guiding hand if desired by grasping an elongated body of the implantation device. Furthermore, the surgical device being secured is held in general alignment with the implantation device so that the proper alignment for screw itself is maintained. This allows the surgeon to operate without resecting tissues to an extent to permit a hand to be close to the implantation site for holding the screw or maintaining the screw in desired and proper alignment.

In accordance with another aspect, release of the implantation device from the implanted surgical device does not affect the position or securement of the surgical device. As noted, the fixation device is commonly a screw rotationally driven into bone such as a vertebra. The discussed prior art utilizes a threaded connection for joining the driver with the coupling element. As such, disconnecting the driver from the coupling element requires counter-rotation from the direction in which the screw is secured with bone. The present implantation device is inserted within and removed from the coupling device in a linear motion so that removal therefrom does not require rotating the implantation device in a manner that may cause the fixation device, or screw, to back out of the bone in which it is secured. Furthermore, a locking actuator member is linearly advanced to shift, generally in a linear direction, locking portions of the implantation device to lock with the surgical device for general immobilization. To release the device, the locking actuator in the form of a rod actuator is simply linearly retracted from the advanced position, thereby allowing the locking portions to release from the surgical device, and then the entire implantation device may be linearly removed from the surgical device.

In accordance with a further aspect, the implantation device does not restrict the surgical device to a limited type of closure member. A coupling device used with, for instance, spinal surgery to receive an elongated member such as a spinal rod for securing the rod with the pedicle portion of a vertebra commonly utilizing a pair of walls, or a yoke-like structure, for receiving the spinal rod therein. To retain and secure the spinal rod therein, the yoke is joined with a closure member. While the discussed coupling element of the prior art system utilizes a threaded connection shared by the driver and the closure element, the present implantation device requires only structure in the coupling device for joining with the locking portion of the implantation device. In the preferred embodiment, this structure is a recess for receiving the locking portion. In a more preferred embodiment, this recess is also utilized by other tools or devices, such as a rod persuader used for seating the spinal rod within the yoke walls and/or a tool for directing and securing the closure member for connection with the surgical device. Accordingly, the structure provided between and on the yoke walls is not dictated by the connection required by the implantation device, and the interior of the yoke walls may be provided with a connection structure for receiving a closure member therebetween, particularly a non-threaded connection structure.

The present implantation device, accordingly, further permits the avoidance of threaded connections between closure members and coupling devices. It is presently believed that a threaded connection requires a greater axial length for the coupling device to be properly and securely joined with the closure member. The use of threads by the prior art system therefore requires a greater axial length then other connection designs, and this greater axial length increases the size of the surgical device and increases the effects of the surgical device when implanted in a body with surrounding tissues and with bio-mechanical motion.

BRIEF DESCRIPTION OF THE DRAWINGS

FIG. 9 is a second side elevational view rotated ninety degrees from the position of FIG. 3 showing the coupling member, the screw anchor, and the driver extensions received between the upstanding walls of the coupling member;

FIG. 10 is a cross-sectional view corresponding to FIG. 9 showing the drive prongs engaged within the screw head recesses;

DESCRIPTION OF THE PREFERRED EMBODIMENTS

Figure 1:
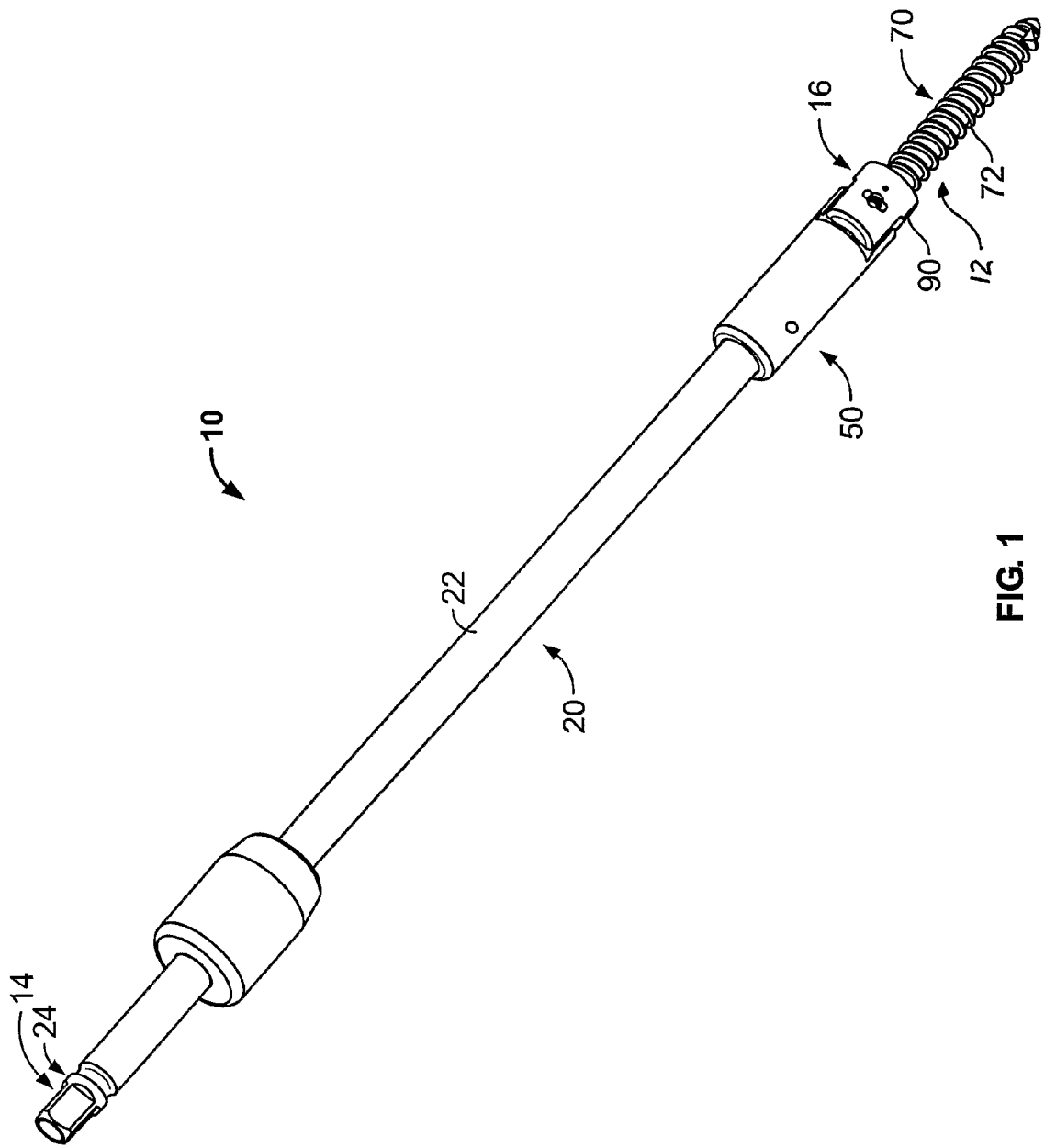
FIG. 1 is a perspective view of a driver apparatus coupled to a spinal rod fixation device at a lower drive end portion of the apparatus.
Figure 2:
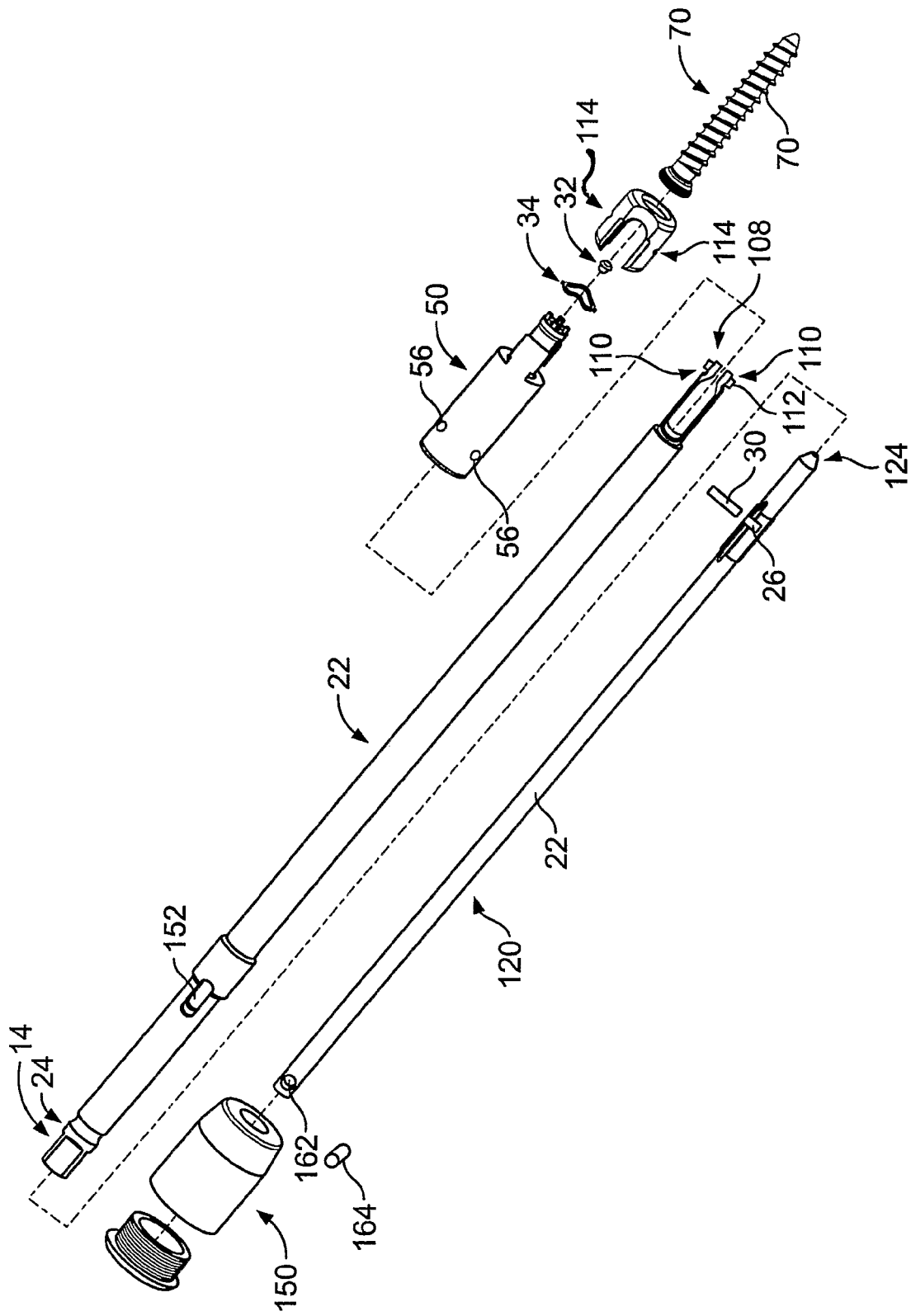
FIG. 2 is an exploded perspective view of the driver apparatus and fixation device of FIG. 1 showing components of the driver apparatus for coupling with an anchor member and with a coupling member of the fixation device.
Figure 3:
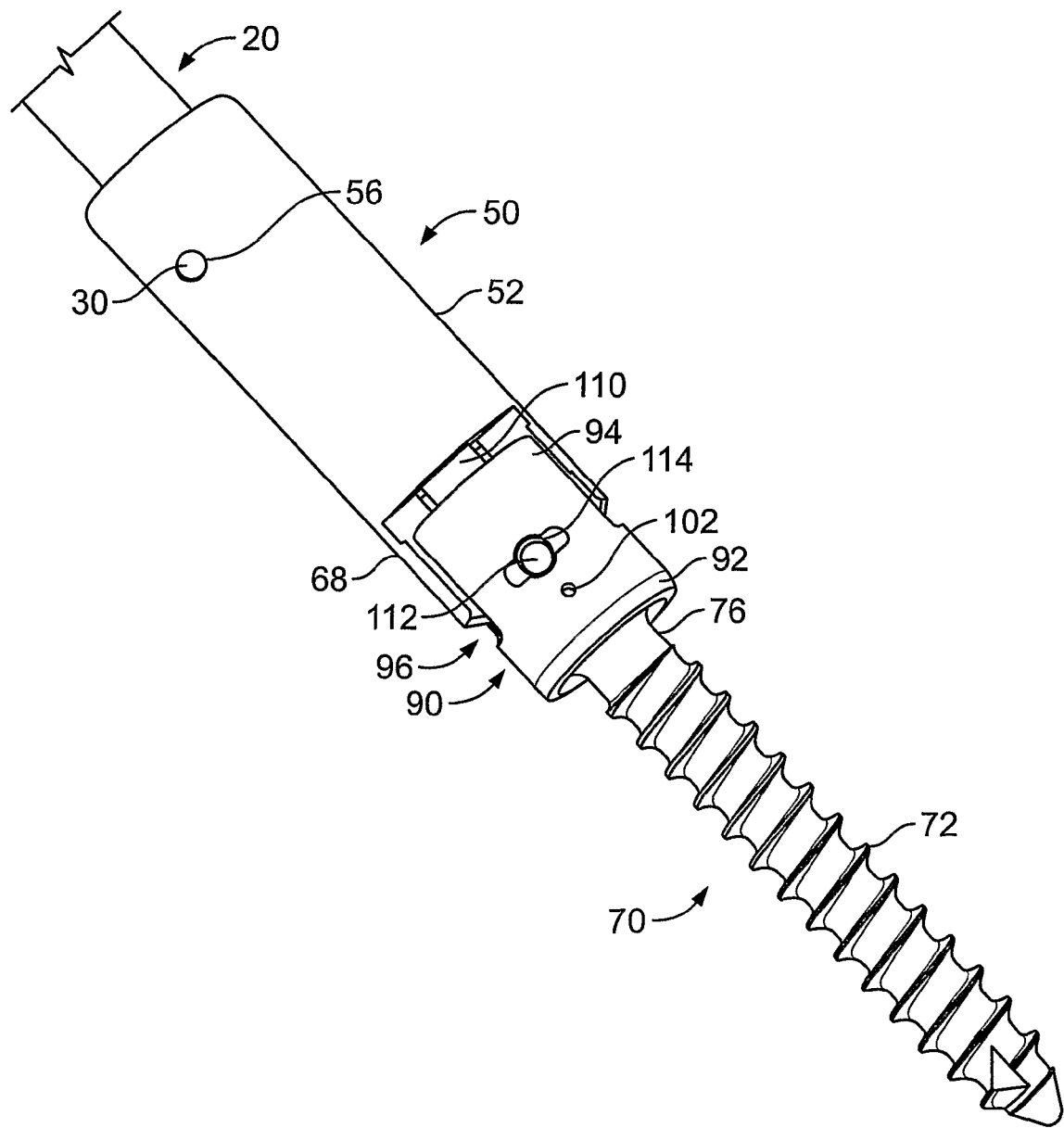
FIG. 3 is an enlarged side view of a distal portion of the driver end portion showing side arms fitting in openings of the coupling member and one of a pair of holding lugs in an associated slots of the coupling member.
Figure 4:
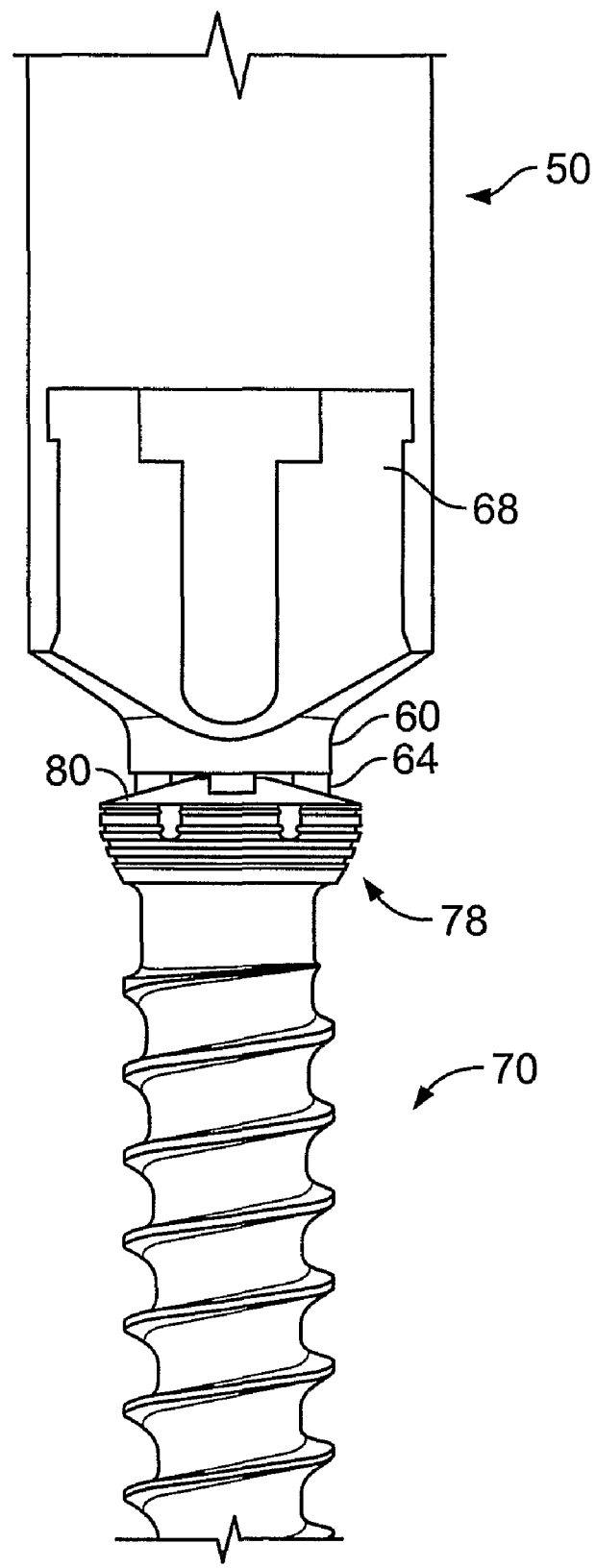
FIG. 4 is a fragmentary side elevational view of the driver end portion showing drive prongs engaged recesses in the screw head.
Figure 5:
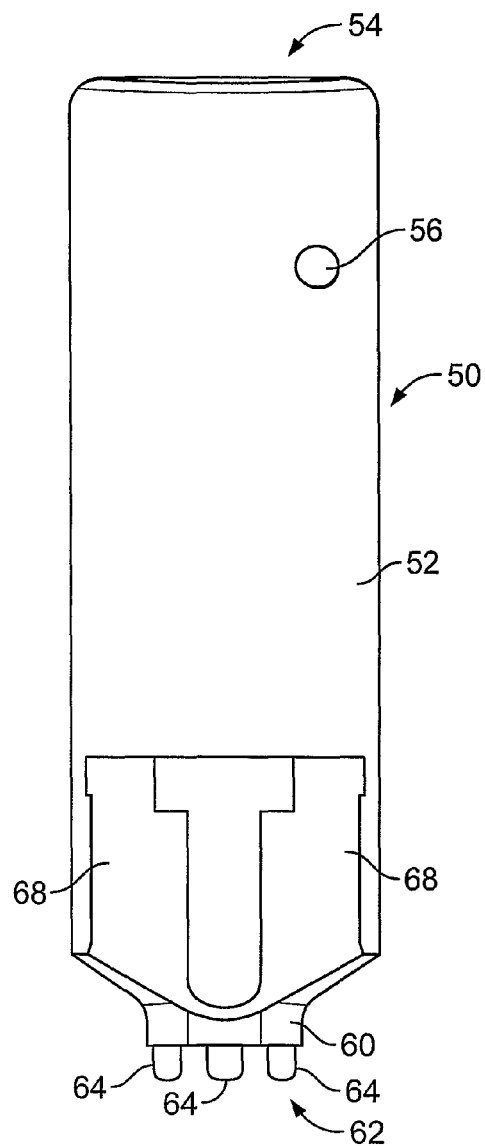
FIG. 5 is a first side elevational view of the driver showing a driver body and a pair of spaced-apart extensions extending from the body.
Figure 6:
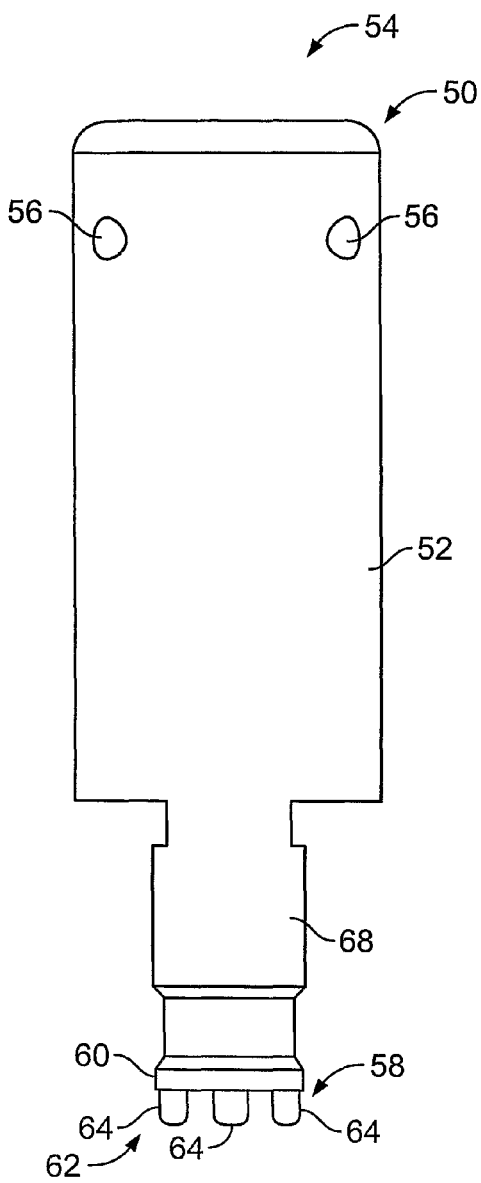
FIG. 6 is a side elevational view of the driver rotated ninety degrees from the position of FIG. 5 and showing the profile of the extensions for being received between the upstanding walls of the coupling member.

Referring initially to FIG. 1, a driving apparatus 10 is depicted for securing a fixation device 12 to a bone such as a vertebra. The implantation device 10 includes a proximal end portion 14 coupled with an operator handle (not shown) and a distal drive end portion 16 for being coupled with the fixation device 12.

The driving apparatus 10 includes a locking member 20 having a body 22 extending between the proximal end 14 and the distal end 16. The locking member 20 adjacent the proximal end 14 includes a non-circular end portion 24 for joining with the operator handle. For instance, the operator handle may include a socket (not shown) for receiving the end portion 24 so that rotation of the operator handle effects rotation of the locking member 20 and the implantation device 10.

The locking member body 22 is generally fixed with the drive end portion 16 of the apparatus 10 so that they are fixed for rotating together so that turning of the locking member 20 causes turning of the drive member 50 including drive prongs 64 thereof about a central axis. As shown, the drive end portion 16 is a driver member 50 connected to a distal end 108 of the locking member 20. In the illustrated form, the locking member body 22 includes a recess 26 such as a notch cut into the side of the locking member body 22 so as to form a surface 28, which is preferably flat. The driver 50 includes a cylindrical body 52 defining an internal bore 54. The driver body 52 has a pair of bores 56 aligned with each other and to one side of the central longitudinal axis, that is, offset from a diameter of the driver body 52 and the locking member body 22. The locking member body 22 is inserted into the driver bore or cavity 54 such that the recess 26 is aligned with the bores 56. The driver 50 and locking member 22 are then generally secured relative to each other by inserting a pin 30 through the bores 56 and into the recess 26 so as to abut the surface 28. In this manner, the driver 50 and locking member 20 may not be separated or rotated relative to each other without removal of the pin 30.

The driver 50 engages the fixation device 12 to secure the fixation device 12 with a bone such as a vertebra. In the illustrated form, the fixation device 12 includes an anchor member 70 and a coupling member 90 wherein the anchor member 70 and coupling member 90 are polyaxially coupled and pivotable relative to each. The anchor member 70 may be secured with the vertebra in a position and orientation dictated by the vertebral surface or structure, as well as by access provided to the implantation site on the vertebra. Being polyaxially coupled to the anchor 70, the coupling member 90 maybe positioned and/or oriented relative to the anchor 70 as desired by a surgeon. For instance, the coupling member 90 includes a base 92 and a pair of upstanding walls 94 together defining a channel 96 into which an elongated member such as a spinal rod (not shown) may be seated for coupling together a plurality of fixation devices 12, and the position of the coupling member 90 may be dictated by the necessary position for the spinal rod.

As shown, the anchor 70 is in the form of a screw, though a hook or other device for securing with a bone may alternatively be used. The screw 70 includes a threaded shank 72 for being driven into and secured with the vertebra, a head 74, and a neck 76 extending therebetween. The neck 76 may be cylindrical or may be slightly tapered. The head 74 includes a bottom arcuate surface 78 for seating within the coupling member 90, as will be discussed below, and has a top surface 80 oriented and configured for engaging the driver 50.

As can be seen in FIGS. 4-8, the driver 50 and screw head top surface 80 have cooperating structure allowing the driver 50 to rotational drive the screw head 74 into the vertebra. In the preferred embodiment, the head top surface 80 includes a central recess 82 aligned with a screw central longitudinal axis for receiving a pivoting insert 32 for engaging a spinal rod received in the channel 96 regardless of relative orientation between the coupling device 90 and the screw 70. The head top surface 80 includes a number of drive engagement recesses 84 radially oriented from the screw central axis and central recess 82. The engagement recesses 84 are preferably rectangular in cross-section, though other shapes may be employed.

Figure 8:
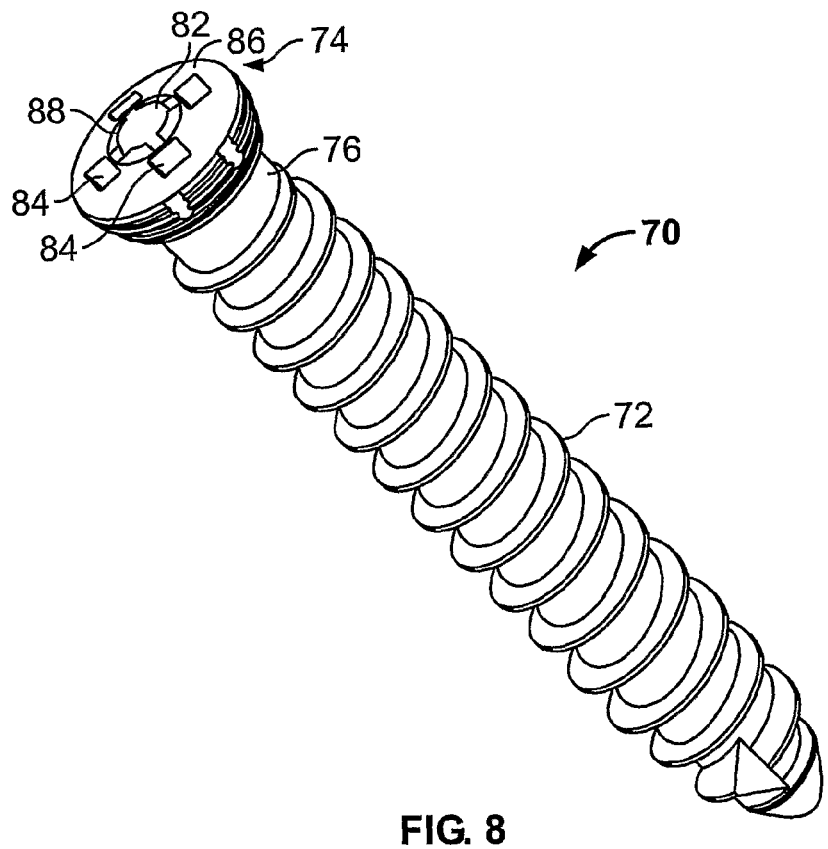
FIG. 8 is a perspective view of the fixation device in the form of a screw having a threaded shank, and a head having a plurality of recesses for cooperating with the driver engagement structure.
Figure 11:
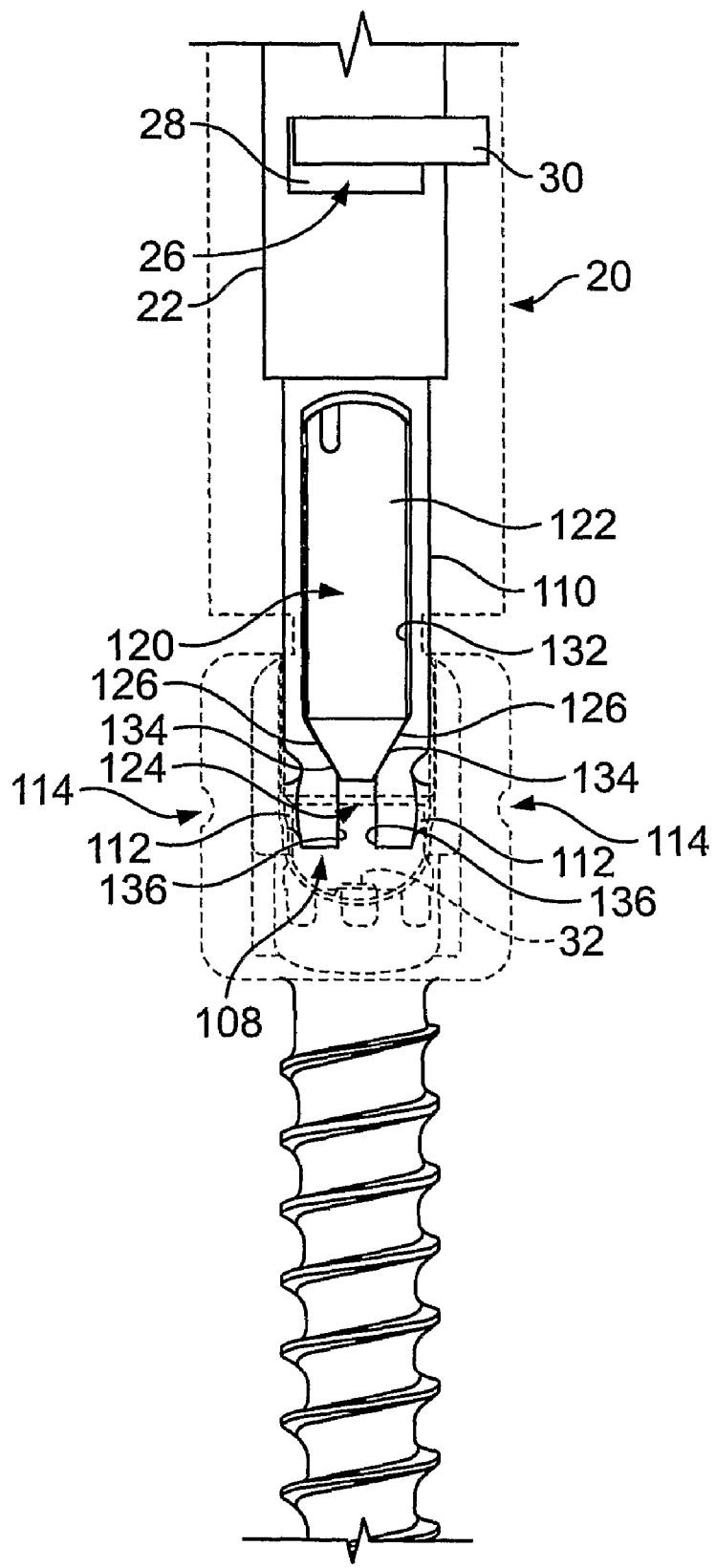
FIG. 11 is a side elevational view of a locking member having a body and locking extensions extending from a distal end thereof, a rod actuator including an end configured for forcing the locking extensions outward for engaging lugs thereon within the upstanding wall recesses, the driver in phantom, and the coupling member with the screw inserted therein.

It should be noted that FIG. 8 depicts the screw head 74 including a plurality of stakes or tabs 88 surrounding and extending over the central recess 82. During assembly, the tabs 88 extend away from the screw head top surface 80 generally parallel to the longitudinal axis of the screw 70. The pivotable insert 32 is positioned in the central recess 82, and the tabs 88 are then deformed to the position shown in FIG. 8 to retain the insert 32 therein while permitting the insert 32 to pivot as desired.

Figure 7:
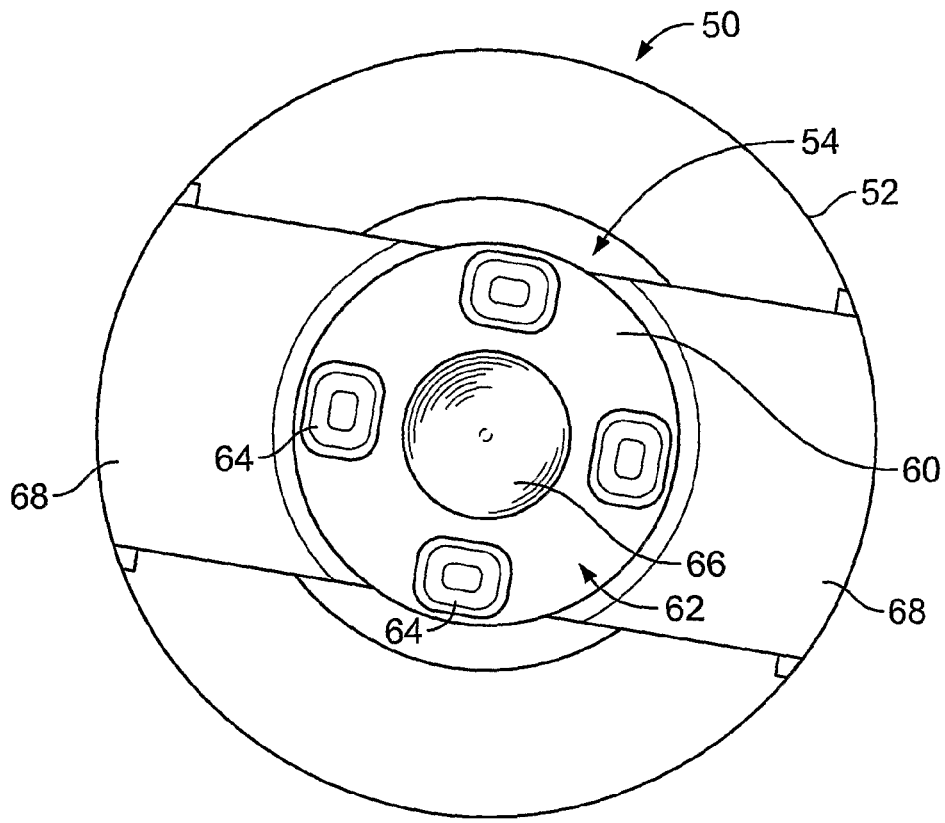
FIG. 7 is an end view of the driver showing drive prongs for cooperating with the fixation device for driving the fixation device into a bone, and showing a central longitudinal bore through the driver body.

The driver 50 mates with the screw head engagement recesses 84 to provide rotational drive to the screw 70. A distal end 58 of the driver 50 includes a plate 60 from which engagement structure 62 protrudes. In the depicted form, the engagement structure 62 includes a plurality of engagement prongs 64 with a shape corresponding to the screw head engagement recesses 84, such as rectangular in cross-section. As can be seen in FIG. 7, the plate 60 includes a depression or recess 66 along a driver central longitudinal axis, the driver 50 thereby allowing clearance for the insert 32 received within the screw head central recess 82 and the crest of the screw head top surface 80 from which the insert 32 may slightly protrude. Accordingly, the mated prongs 64 and engagement recesses 84 require the co-rotation of the driver 50 and the screw 70.

To enable the driver engagement structure 62 to mate with the screw head recesses 84, the driver distal end 58 is configured for being received in the channel 96 and between the upstanding walls 94, as can be seen in FIG. 9. The driver 50 includes a pair of extensions 68 extending from the driver body 52. The extensions 68 terminate at and join with the driver plate 60. As shown, the extensions 68 are dimensioned to have a width for closely fitting within and between the upstanding walls 94. Thus, the extensions 68 and upstanding walls restrain relative movement between the driver 50 and coupling device 90. Since the extension 68 fit in the channel 96 between the walls 94, they will engage one side or the other along the channel 96 openings when the driver 50 is turned, depending on the turning direction, so that the coupling member 90, along with the engaged screw anchor 70, turn therewith. In addition, the extension 68 stop the coupling member 90 from pivoting relative thereto, and the engaged screw anchor 70 keeping the coupling member and screw anchor 70 in a substantial co-axial direction.

As noted above, the implanted screw 70 and coupling member 90 may pivot polyaxially relative to each other for receiving a spinal rod having a desired orientation. Towards this end, the head 74 includes the bottom arcuate surface 78 for seating within the coupling member 90. As shown in FIG. 10, the coupling member base 92 includes a bore 98 aligned with a central axis of the coupling member 90 and a seat 100 surrounding the bore 98. The screw 70 is inserted through the channel 96 so that the threaded shank 72 extends through the bore 98. In general, the contour of the screw head bottom surface 78, the contour of the seat 100, a diameter of the neck 76, and the size and shape of the bore 98 determine the amount of polyaxial motion permitted between the screw 70 and the coupling member 90. During implantation, the coupling member 90 and the screw 70 are aligned along their central longitudinal axes so as to be in the configuration shown in FIG. 10. It is noted that the coupling member 90, the screw 70, and the driver 50 are configured so that, when the driver 50 is engaged with the screw 70, the extensions 68 of the driver 50 restrict pivoting of the coupling member 90.

The fixation device 12 preferably restricts the ability for the coupling member 90 to shift downward along the screw shank 72. That is, the fixation device 12 includes a retainer 34 inserted within the coupling member 90 in a position to restrict the screw 70 from moving into the channel 96. More specifically, the retainer 34 includes a peripheral or ring portion 36 and retention structure 38 extending outward from the ring 36. The screw 70 is inserted through the bore 98 so that the screw head bottom surface 78 is positioned on or near the seat 100, and the retainer 34 is inserted through the channel 96 so that the ring portion 36 rests on a peripheral portion 86 of the screw head top surface 80. During insertion, the retainer 34 is compressed slightly to provide clearance for the retention structure 38. At a predetermined depth of insertion for the retainer 34, the retention structure 38 aligns with ports or other recesses 102 located on the interior of the upstanding walls 94, as can be seen in FIG. 10. The retainer 34 is resiliently deformable to permit the polyaxial motion described above for the coupling member 90 and the threaded shank 70, and may be deformed either prior to insertion or due to insertion to restrict the coupling member 90 from falling down the screw shank 72, as shown in FIG. 10.

Figure 12:
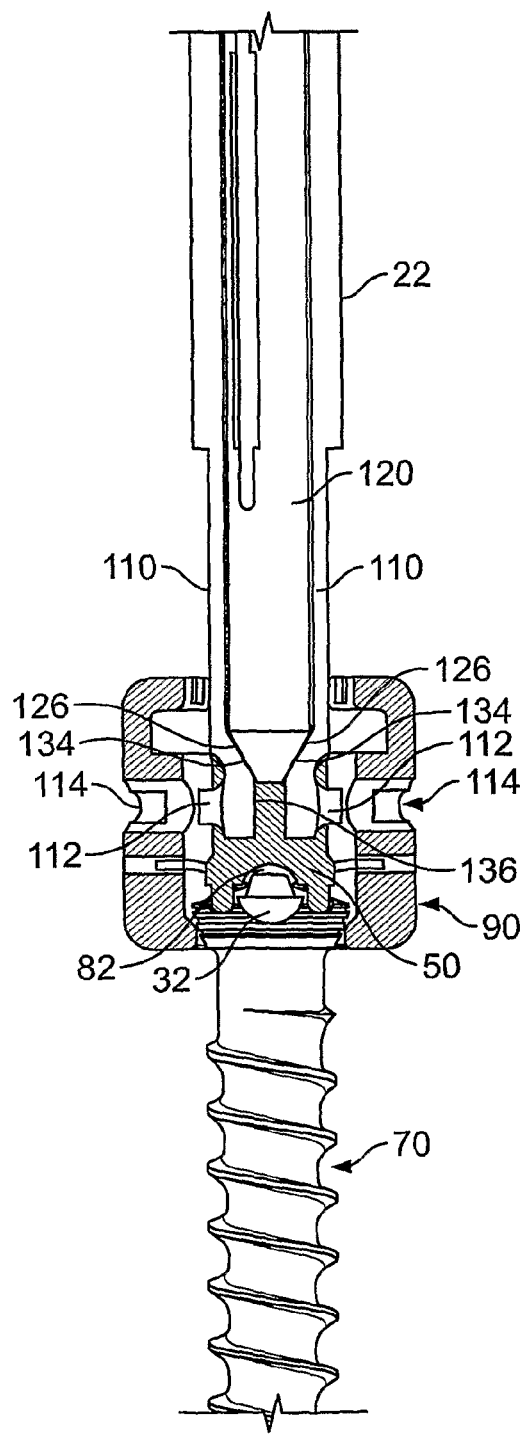
FIG. 12 is a cross-sectional view showing the lugs positioned between the upstanding walls for being received by the recesses thereof.

After the driver 50 is engaged with the screw 70, the locking member 20 is interlocked with the coupling member 90 to generally immobilize the coupling member 90 relative to the screw 70. A distal end 108 of the locking member 20 includes a pair of extensions or arms 110 extending from the locking member body 52 and between the coupling member walls 94. The arms 110 have lugs 112 extending laterally or radially outward therefrom a short distance. The driver 50 is inserted within the coupling member 90 to a predetermined depth to bring the lugs 112 into alignment with recesses or ports 114 formed in the coupling device walls 94, as shown in FIG. 12. The retainer 34 permits the polyaxial movement between the screw 70 and coupling member 90, it may be necessary to draw the coupling member 90 towards the proximal end 14 of the driving apparatus 10 to achieve the proper alignment of the lugs 112 with the ports 114.

Figure 13:
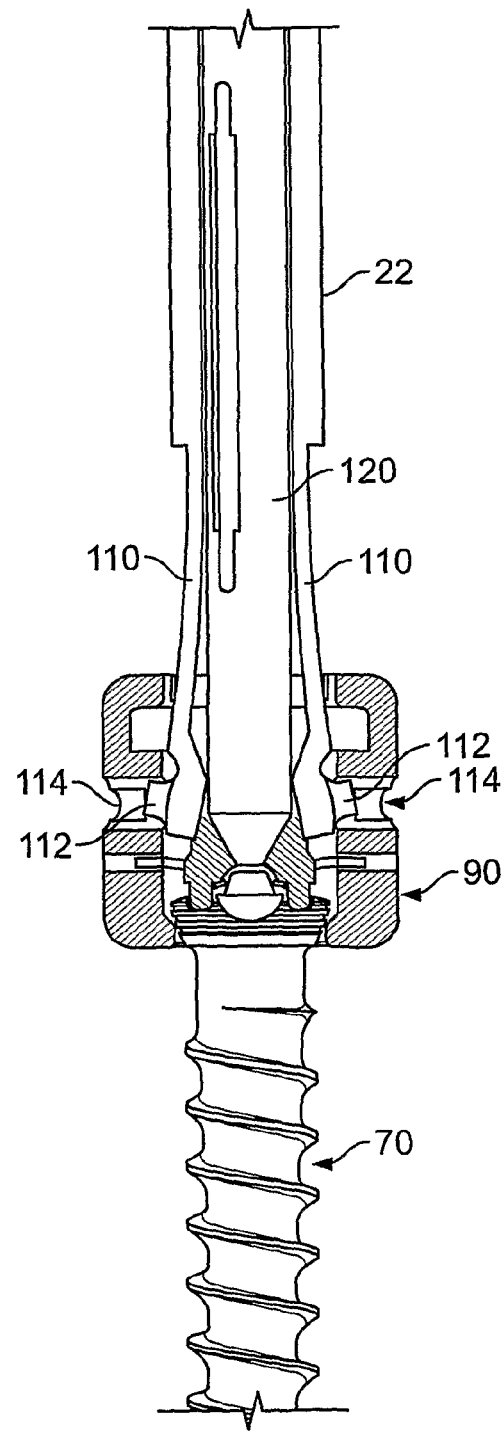
FIG. 13 is a cross-sectional view corresponding to FIG. 12 showing the rod actuator and locking member in a locked position, the rod actuator being advanced to force the locking member extensions outward such that the lugs engage with the upstanding wall recesses.
Figure 14:
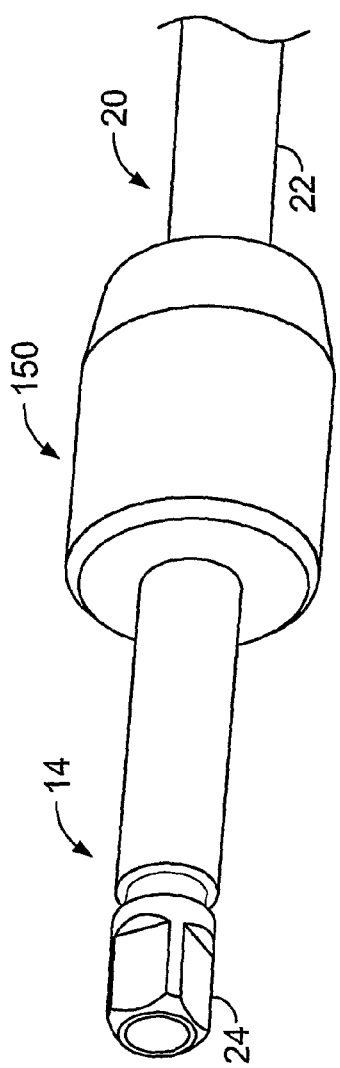
FIG. 14 is a perspective fragmentary view of a proximal end of the apparatus showing the locking member body and a handle for selecting the position of the rod actuator for locking and unlocking the locking apparatus with the fixation device.
Figure 15:
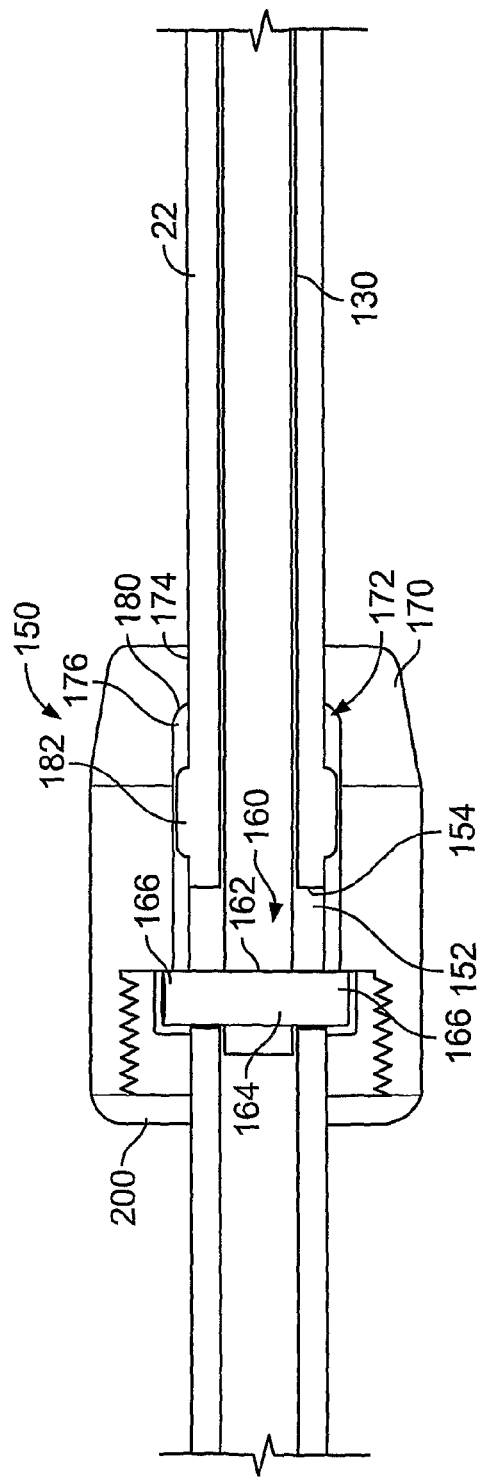
FIG. 15 is a fragmentary cross-sectional view of the locking member body having a slot receiving a pin secured with the rod actuator, and the handle secured on the pin and on a shoulder formed on the locking member body such that movement of the handle in a longitudinal direction of the locking member body shifts the rod actuator between the locked and unlocked positions.
Figure 16:
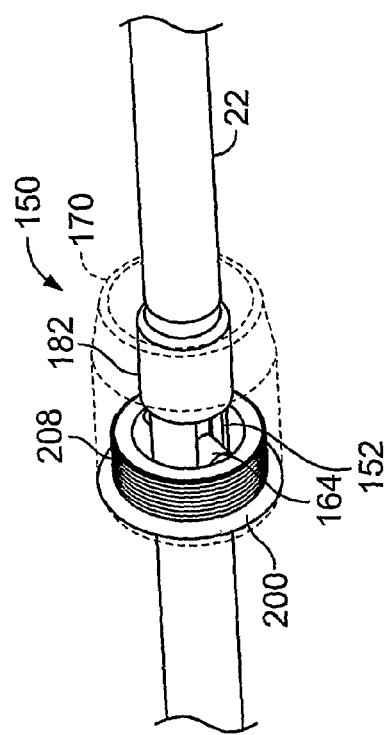
FIG. 16 is a fragmentary perspective view of the proximal end showing a first handle portion having an annular portion threadably received by a sleeve handle portion, the handle portions securing the pin therebetween.
Figure 17:
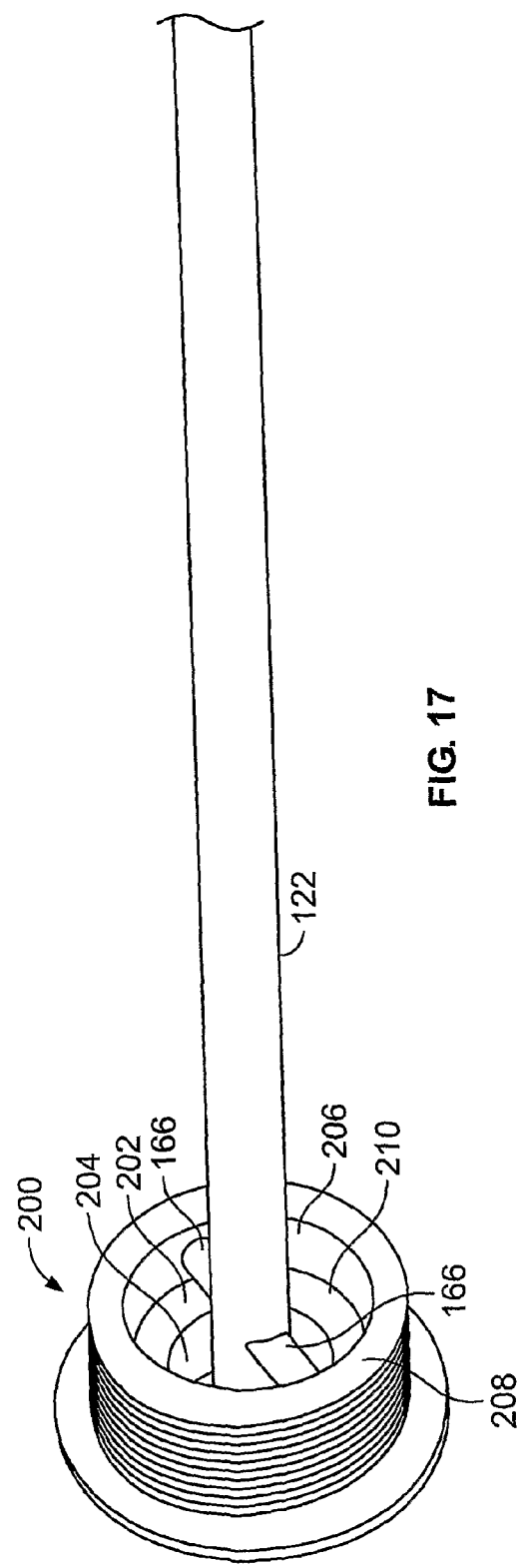
FIG. 17 is a perspective view of the first handle portion showing the pin abutting a shoulder formed within the annular portion, and the pin received within a bore of the rod actuator.

With the drive prongs 64 received in the drive recesses 84 of the screw head 74, the longitudinal axes of the screw 70 and coupling device 90 will be in substantial alignment. This alignment then allows the lugs 112 to be aligned with the ports 114 for being pushed through and holding the coupling member 90 against shifting relative to the drive member 50, as shown in FIG. 13.

The fixation device 10 utilizes an actuating rod 120 cooperating with the locking member 20 to direct the lugs 112 into the ports 114. The actuating rod 120 may be shifted between extended and retracted positions corresponding to locked and unlocked configurations for the driver apparatus 10 with the fixation device 12. The unlocked configuration is illustrated in FIG. 12 with the lugs 112 positioned outside of the coupling member wall ports 114, while the locked configuration is shown in FIG. 13 with the lugs 112 received within the ports 114.

The locking member 20 includes a central longitudinal bore 130 within which the actuating rod 120 is received. The actuating rod 120 may be reciprocated or actuated for movement along its longitudinal axis to and between the retracted and advanced positions. As noted, the arms 110 extend from the locking member body 52, and they are positioned generally to permit reciprocation of the actuating rod 120 therebetween. However, the arms 112 have respective inboard sides 132 facing each other. Each inboard side 132 includes a ramp surface 134 extending inwardly in the distal direction and towards the respective ramp surface 134 of the opposed arms 114. Each ramp 134 terminates at a flat 136 positioned generally on the inboard side 132 opposite the lugs 112.

To lock the lugs 112 in the ports 114, the actuating rod 120 wedges against the ramps 134. The actuating rod 120 has a generally cylindrical body 122 with a terminal end 124 which may be conical or wedge-shaped to have at least a portion 126 angled from the body 122 and positionable against each of the ramps 134. As the actuating rod 120 is advanced towards the fixation device 12 with the driver apparatus 10 secured thereto, the angled portions 126 bear against and wedge outward the ramps 134 and their associated arms 110 and lugs 112. The actuating rod 120 may be advanced to the locked position in which the lugs 112 are positioned within the ports 114 and the cylindrical body 122 is positioned against and between the flats 136 of the opposed arms 110. More specifically, as the actuating rod 120 is advanced forward, it bottoms out on the driver 50. The engagement of the actuating rod 120 causes the lugs 112 to flex or shift laterally into the parts 114 of the coupling member in order to lock the apparatus thereto.

When moving from the locked position to the unlocked position, the locking rod 120 is retracted. As the locking rod 120 moves away from the ramps 134 and flats 136, the arms 110 and associated lugs 112 shift inward so that the lugs 112 are released from the ports 114. To enable this motion, the arms 110 have a flexibility so that, when the locking rod 120 is retracted, the arms 110 shift inward to a natural position. The treading of the actuator rod 120 to the locking member 20 searves to generally retard or inhibit unintentional retraction of the actuating rod 20.

Referring now to FIGS. 14-18, the driver apparatus 10 includes a handle or grip 150 for selecting the position of the actuating rod 120 and, thus, the unlocked and locked positions of the driver apparatus 10 with the fixation device 12. As noted above, the actuating rod 120 is received within a bore 130 of the locking member body 22. The bore 130 extends from the arms 110 to a position rearward sufficient for locating the handle 150 on the locking member 20. Preferably, at least one slot 152 is formed in the side of the locking member body 22 at a position desired for generally locating the handle 150. As illustrated, a pair of slots 152 are aligned with each other across a diametral line of the locking member body 22.

The actuating rod 120 includes a pinned portion 160 is which positioned between the slots 152 when the actuating rod 120 is in the advanced, locked position. The pinned portion 160 includes a throughbore 162 for receiving a pin 164 therethrough. The pin 164 has ends 166 extending through the slots 152 when assembled. The slots 152 may be sized so that the pin 164 contacts a front edge 154 of the slot 152 when the actuating rod 120 is fully extended. The slots 152 should also be sized so that the pin 164 may shift sufficiently therein to permit full retraction of the actuating rod 120 from between the ramps 134 and flats 136 of the locking member arms 110.

The grip member 150 secures with the pin 164 for shifting the actuating rod 120 between the locked and unlocked positions. The grip 150 includes an outer grip portion 170 and an inner grip portion 200 secured together to capture the ends 166 of the pin 164. The outer grip portion 170 is a sleeve-like member defining an internal cavity 172. The cavity 172 includes a first portion 174, a second portion 176, and a third portion 178 along its axial length. The first portion is sized closely to the locking member body 22, though with appreciable clearance so that the first portion 174 may use the locking member body 22 as a guide for relative movement without becoming bound therewith.

The second portion 176 of the outer grip cavity 172 is larger in diameter than the first portion 174 so a radial shoulder 180 is formed therebetween. The locking member body 22 includes an enlarged diameter section 182. When assembled, the enlarged section 182 is generally positioned within the second cavity portion 176. When the handle 150 and actuating rod 120 are retracted, the shoulder 180 may serve as a stop indicating full retraction thereof.

Figure 18:
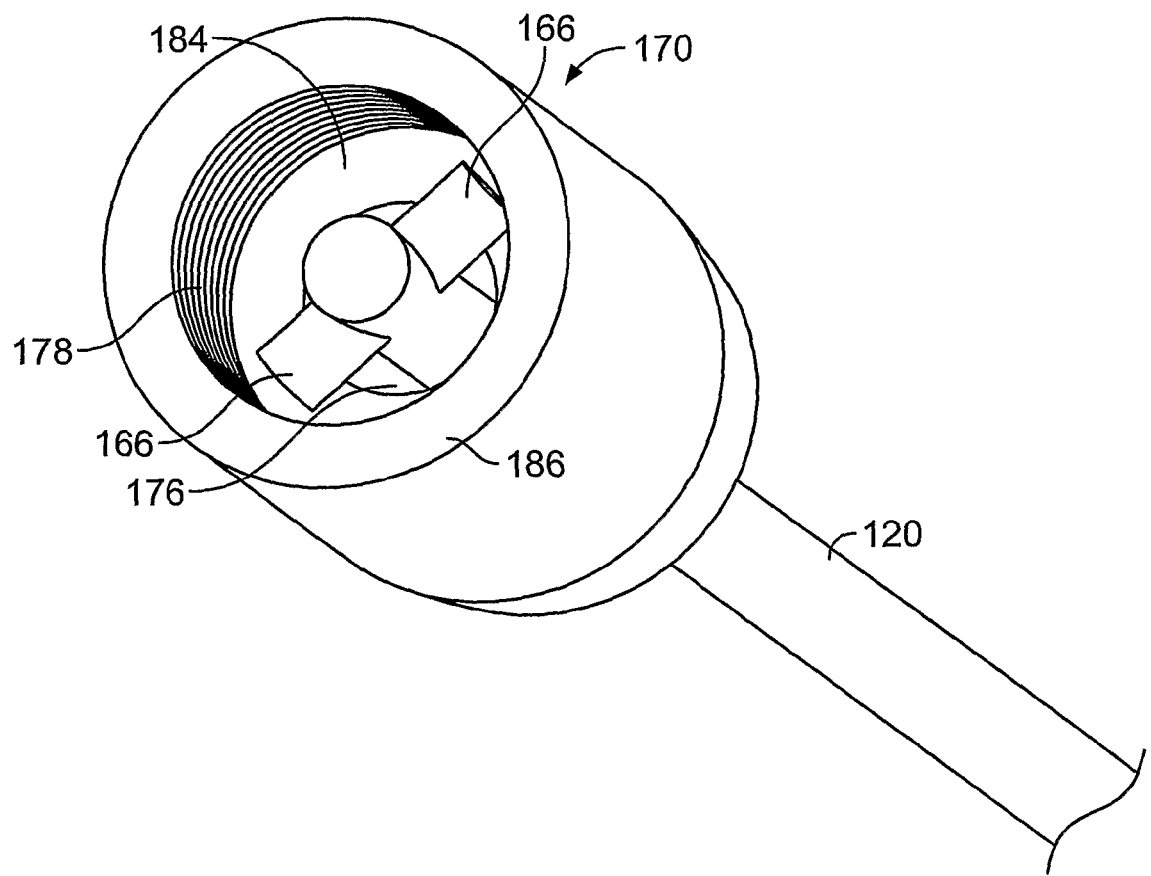
FIG. 18 is a perspective view of the sleeve handle portion showing the pin abutting a shoulder formed within the sleeve.

The outer grip third cavity portion 178 (FIG. 18) has a larger diameter than the second portion 176 so that the junction therebetween forms a second shoulder 184. As can be seen in FIG. 18, the pin 164 is positioned against the shoulder 184 and within the third portion 178 when assembled. More particularly, the pin 164 and its ends 166 are positioned within an internally threaded annular portion 186 extending about the third cavity portion 178.

The inner and outer grip portions 170, 200 capture the pin ends 166 therebetween. The inner grip portion 200 has a cavity 202 having a first portion 204 sized to utilize the locking member body 22 as a guide, and a second portion 206 sized so that the annular wall 208 extends about the pin 164. The annular wall 208 is externally threaded so that it may be threadably joined to the internally threaded annular wall portion 186 of the outer grip portion 200. The second cavity portion 206 is larger in diameter than the first cavity portion 204 so that a shoulder 210 is formed between the two cavity portions 204, 206. When the inner and outer grip portions 170, 200 are threaded together, the pin 164 is positioned and captured between the shoulders 184, 210. Accordingly, when the grip 150 is slidably moved along the locking member body 22, it causes the actuating rod 120 to reciprocate between the locked and unlocked positions with the pin 164 traveling in the guide slots 152 of locking member body 22. The pin 164 is a guide pin that cooperates with the guide slots 152 to define limits of retracting and advancing movements of the actuating rod 120.

In operation, the driver apparatus 10 is inserted by linear motion directly into an upwardly facing opening of the coupling member 90 so that the driver 50 engages with the screw 70 with the prongs 64 received in the engagement recesses 84 of the screw head 74, the coupling member 90 and screw will be co-axially oriented and the locking lugs 112 will be aligned with the ports 114 of the opposed coupling member walls 94. The actuating rod 120 is then advanced forward, towards the screw 70, to force the lugs 112 into engagement with the coupling member ports 114 and to lock the coupling member 90, screw 70, and driver apparatus 10. The entire assembly may then be rotated to drive the screw 70 into the vertebra. To disconnect the driver apparatus 10 from the implanted fixation device 12, the actuating rod 120 is retracted to release the lugs 112 from the ports 114. The driver apparatus 10 may then be retracted by linear motion. Accordingly, the motions for disconnecting the driver apparatus 10 from the implanted fixation device 12 do not require rotation that may otherwise back the screw 70 out of the vertebra.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. A driver apparatus comprising:
    a drive shaft assembly having proximal and distal ends, a longitudinal axis extending therebetween, and a throughbore extending axially along the longitudinal axis;
    at least one resilient locking arm of the drive shaft assembly configured to be shifted outwardly away from the longitudinal axis to a locked position;
    drive structure at the distal end of the drive shaft assembly that projects axially beyond the resilient locking arm for mating with corresponding drive structure of a screw anchor;
    an elongate actuating rod configured to fit into the throughbore and having a predetermined actuating position in the throughbore so that when advanced thereto the actuating rod is axially spaced from the drive structure of the drive shaft assembly and the screw anchor mated therewith; and
    a distal end of the actuating rod configured to urge the resilient locking arm to the locked position thereof for being lockingly engaged with a pivotable member coupled to the screw anchor as the actuating rod is advanced to the predetermined actuating position thereof.

2. The driver apparatus of claim 1 wherein the resilient locking arm and the actuator rod distal end have cooperating cam surfaces that cammingly engage each other to urge the locking arm to the locked position thereof as the actuating rod is advanced to the predetermined actuating position thereof.

3. The driver apparatus of claim 1 wherein the drive shaft assembly includes an elongate body having proximal and distal ends, and the at least one resilient locking arm comprising a pair of opposite resilient locking arms at the elongate body distal end, and the drive shaft assembly further includes a drive member connected to the elongate body and having a central bore through which the elongate body extends so that the locking arms project out therefrom and having a bottom distal end having the drive structure formed thereon to extend axially beyond the locking arms.

4. The driver apparatus of claim 1 wherein the drive structure includes a plurality of axially extending prongs circumferentially spaced about the longitudinal axis.

5. The driver apparatus of claim 1 in combination with a spinal rod fixation apparatus including the screw anchor for being anchored in a vertebral bone and wherein the pivotable member is a coupling member of the spinal rod fixation apparatus for having a spinal rod locked therein.

6. The combination of claim 5 wherein the at least one locking arm comprises a pair of opposite locking arms each having a locking lug extending laterally outward therefrom, and the coupling member includes a pair of upstanding walls each having an aperture with the locking arms having an unlocked position where the locking arms fit between the upstanding walls and in the locked position the locking arms are urged outwardly so that the locking lugs thereof are received in the corresponding apertures of the upstanding walls.

7. The combination of claim 6 wherein the coupling member upstanding walls include vertical slots therebetween, and the drive shaft assembly includes extensions that extend along the locking arms and fit into the vertical slots with the drive structure extending distally below the extensions so that the extensions cooperate with the locking arms shifted to the locked positions thereof to cause the coupling member to be rotated with the screw anchor upon rotation of the drive shaft assembly for driving the screw anchor into a vertebral bone.

* * * * *